(12) United States Patent
Wang

(10) Patent No.: US 6,413,281 B1
(45) Date of Patent: Jul. 2, 2002

(54) 2-(P-SULPHOPHENYL)AMINO-1,3,5-TRIAZINE DERIVATIVE AND THE SALT OF ALKALI METAL THEREOF, A PROCESS FOR THE PREPARATION AND THEIR USE AS AN AUXILIARY OF CATIONIC DYE

(76) Inventor: Zhi Wang, 27-A604, Xiangxi Huayuan, Ningxilu, Xiangzhou District, Zhuhai, Guangdong 519000 (CN)

( * ) Notice: Subject to any disclaimer, the term of this patent is extended or adjusted under 35 U.S.C. 154(b) by 0 days.

(21) Appl. No.: 09/485,945

(22) PCT Filed: Sep. 7, 1999

(86) PCT No.: PCT/CN99/00140

§ 371 (c)(1),
(2), (4) Date: Feb. 17, 2000

(87) PCT Pub. No.: WO00/21939

PCT Pub. Date: Apr. 20, 2000

(30) Foreign Application Priority Data

Oct. 12, 1998 (CN) ................................ 98120095.8 A
Oct. 12, 1998 (CN) ................................ 98120096.6 A
Oct. 12, 1998 (CN) ................................ 98120097.4 A

(51) Int. Cl.[7] ............................. D06P 3/14; D06P 1/41; D06P 1/62
(52) U.S. Cl. ........................ 8/529; 8/566; 8/654; 8/657; 8/917; 8/930
(58) Field of Search ............................ 8/529, 566, 654, 8/657, 917, 930; 544/194, 208, 211, 216, 218, 217, 219

(56) References Cited

U.S. PATENT DOCUMENTS 5,495,003 A  2/1996 Pedrazzi et al.

FOREIGN PATENT DOCUMENTS

GB  2160883 A  1/1986
GB  WO 94/22961  10/1994

*Primary Examiner*—Margaret Einsmann
(74) *Attorney, Agent, or Firm*—Hogan & Hartson, L.L.P.

(57) ABSTRACT

2-(p-sulphophenyl) amino-1,3 5-triazine derivatives [1] and their alkali salts, wherein $R_1$, represents Cl, F; $R_2$ is α- or β-naphthylamino, or α- or β-naphthoxy, and the method for preparing the compound are provided. The compound can be used as a cationic dye auxiliary agent in dyeing animal protein fibers (such as wool, cony hair, camel hair and natural silk) and their textile fabric as well as blended yarn or fabric containing the animal protein fiber.

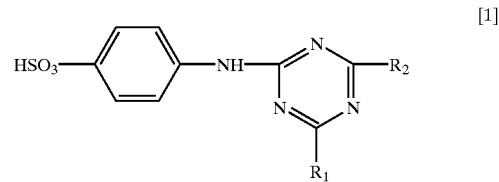

[1]

8 Claims, No Drawings

2-(P-SULPHOPHENYL)AMINO-1,3,5-TRIAZINE DERIVATIVE AND THE SALT OF ALKALI METAL THEREOF, A PROCESS FOR THE PREPARATION AND THEIR USE AS AN AUXILIARY OF CATIONIC DYE

FIELD OF THE INVENTION

The present invention relates to novel 2-(p-sulphophenyl) amino-1,3,5-triazine derivatives and to their use in dyeing animal protein fibers (such as wool, cony hair, camel hair and natural silk) and their textile fabric as a cationic dye auxiliary agent.

BACKGROUND OF THE INVENTION

For a long time it has been known to use acid dyes (including weak acid dyes), acid mordant dyes or reactive dyes to dye animal protein fibers, such as wool, natural silk and so on. For example, CN1040643A disclosed that acid mordant dyes were used to dye textile fabric, that mordant NaCN was used for the mordant dyeing process, and that compound of formula [10] was used to partially replace NaCN for the mordant dyeing process. In CN1035536A, it was mentioned that acid mordant was used to dye protein fibers with the addition of mixed chlorinates of rare elements, formic acid, etc.

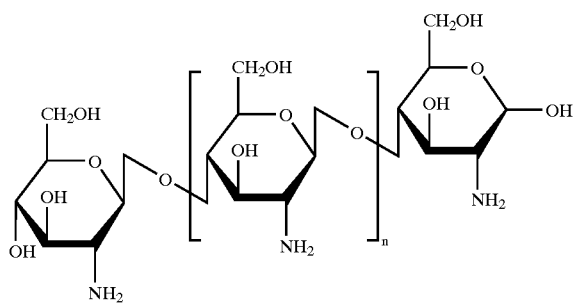

[10]

Up to now, the methods of dyeing animal protein fibers by use of acid dyes (including weak acid dyes), acid mordant dyes or reactive dyes still exhibit the following shortcomings. 1) The method cannot achieve high dyeing quality, i.e., the color is not bright enough and the color fastness is not sufficient. 2) In the dyeing and finishing process, use of a great amount of strong acids and hypertoxic chemicals (for example, NaCN) heavily impairs the environment and human health. 3) During the dyeing and finishing process, the cost increases by using varied dye auxiliary agents, such as penetrating agents, diffusing agents, softeners and so on, which, at the same time, cause heavy environmental pollution.

The cationic dyes developed afterwards are especially for acrylic fibers. The dyes are bonded together with fibers mainly through ionic bonding and/or covalent bonding. Although cationic dyes have a complete range of color spectra, a satisfactory variety of color, and bright color and high color fastness, they could not be used to dye and finish animal protein fibers.

Due to the aforementioned reasons, the stage-dyeing process should be used for dyeing blended yarn or blended fabric which contains animal protein fiber and synthetic fiber by using different kinds of dyes, i.e., dyeing the synthetic fiber and then dyeing the animal protein fiber, or dyeing the animal protein fiber first and then dyeing the synthetic fiber. The process needs a long time to complete by using a large amount of dyes with a subsequent high cost.

The object of the present invention is to provide a cationic dye auxiliary agent so that it is possible to use cationic dyes for dyeing and finishing animal protein fibers.

The present invention further provides a process for preparing the cationic dye auxiliary agent.

The invention further provides the application of such a cationic dye auxiliary agent when cationic dyestuffs are used to dye and finish animal protein fibers.

This invention also provides a process for dyeing and finishing animal protein fibers by using cationic dyestuffs through the cationic dye auxiliary agent.

DESCRIPTION OF THE INVENTION

The objects of the invention are achieved by providing novel 2-(p-sulphophenyl) amino-1,3,5-triazine derivatives of formula [1] and salts thereof, preferably their sodium salts

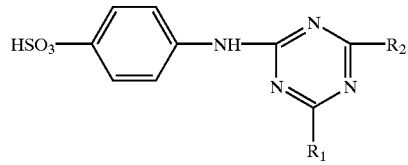

[1]

wherein $R_1$, represents halogen, preferably Cl, F, $R_2$, is α- or β-naphthylamino, α- or β-naphthoxy.

The cationic dye auxiliary agent according to the present invention can be selected from the group of the following compounds (a)~(g) and sodium salt thereof:

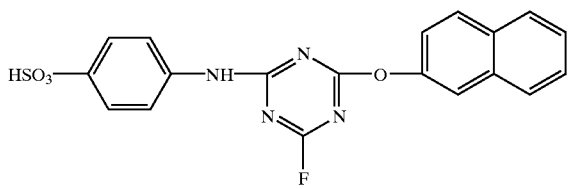

(a)

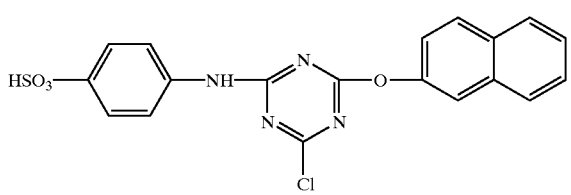

(b)

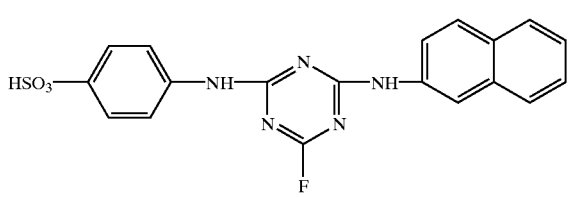

(c)

(d)

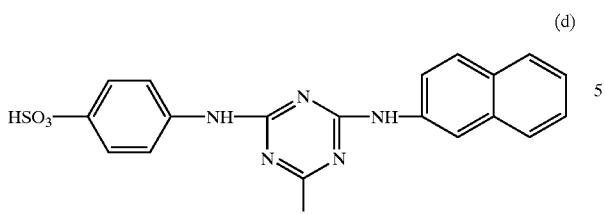

(e)

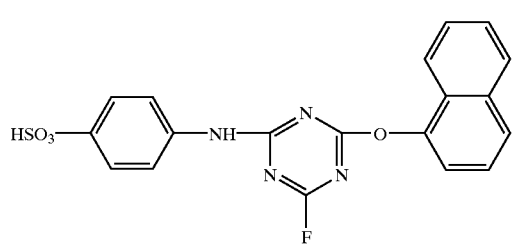

(f)

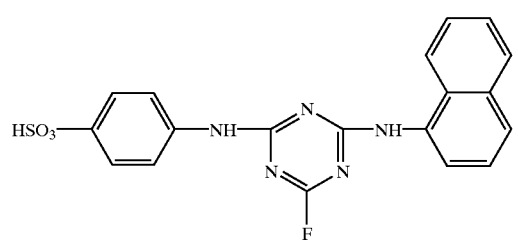

(g)

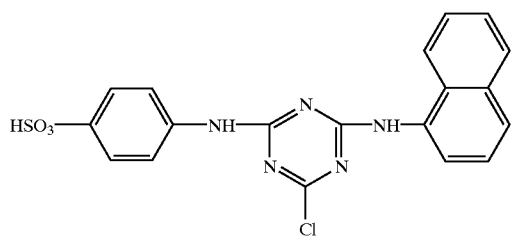

This invention further provides the method for synthesizing the above-described 2-(p-sulphophenyl) amino-1,3,5-triazine derivatives.

The compound of formula [1] can be synthesized according to the following procedures:

Reaction (1)

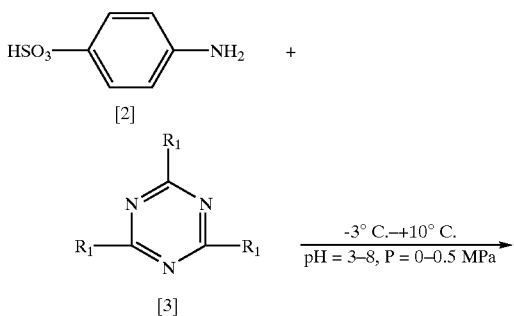

-continued

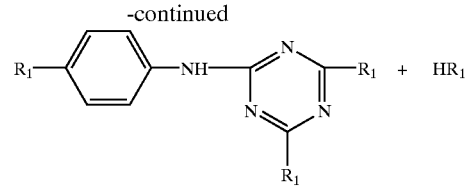

[4]

Reaction (2)

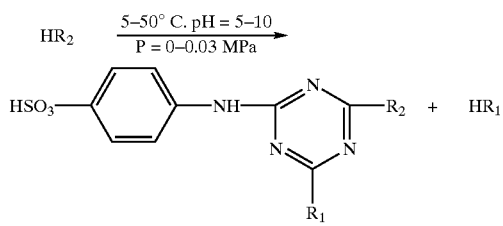

In the above procedures, the compounds of formula [1] are prepared with cyanuric trihalide [3], p-aminobenzene sulfonic acid [2] (or salt thereof) and amino-naphthalene (or naphthol) $HR_3$, as raw materials by a two-step reaction.

Reaction (1): Cyanuric trihalide as formula [3] is dissolved into ice water in a reaction vessel, then p-aminobenzene sulfonic acid as formula [2] or its salt is slowly added into the solution and the reaction is initiated. The temperature is controlled at −3~10° C., and the pressure is between 0 and 0.05 MPa. Then the catalyst, i. e., a mixed solution of sodium hydroxide and phosphoric acid, is added into the reaction solution. The reaction is sustained for 3~5 hrs. When the pH value of the reaction solution exceeds 5 and the amount of free amine is less than 0.8%, the intermediate as formula [4] is obtained.

Reaction (2): The intermediate as formula [4] is moved into another reaction vessel, then a solution of compound $HR_2$ (α- or β-naphthylamino, or α- or β-naphtol) as well as a catalyst, i. e., a mixed solution of sodium hydroxide and phosphoric acid, are added into the same vessel. The reaction is sustained for 4~5 hrs. at a temperature of 15~50° C., under a pressure of 0~0 03 MPa, with pH value of 5~10. When the pH value is adjusted to around 7 by using acetic acid, the compound as formula [1] is finally obtained through discharging, filtering, drying and grinding.

In the above synthetic processes, molar ratios of the three raw materials are controlled within the range as: cyanuric trihalide: p-aminobenzene sulfonic acid or its salt: naphthylamino (or naphthol)=1.0: (1.10~1.3): (1.0–1.25). For reaction (1), the yield of the intermediate as formula [4] is between 87% and 92%, and the yield of product of formula [1] for reaction (2) is 91%~97%.

There is an essential difference between the dye agent according to the present invention and other ones used in the prior art in the dyeing and finishing industry. The dye auxiliary agent used in the prior art only plays a certain role as a dyeing promoter, but does not participate in the chemical reaction of the molecular chain. However, the dye auxiliary agent according to the present invention participates in the chemical reaction of the molecular chain, i.e., one end group of molecules of the dye auxiliary agent chemically reacts with the fiber molecules and the other group reacts with the cationic dye molecules, thus the cationic dye is firmly bonded to the fiber molecule to achieve coloration. The compound according to the present invention plays a role as a link arm. The cationic dye, which formerly could not bind with the protein fiber, thus bonds to the protein fiber by the aid of said link arm.

The present invention further provides the application of the compounds as formula [1] as a cationic dye auxiliary agent when cationic dyestuffs are used for dyeing and finishing animal protein fiber or its fabric as well as blended yarn or its fabric containing animal protein fiber. Herein, said animal protein fibers are such hairs as wool, cashmere, cony hair, and camel hair, as well as natural silk. Blended yarn means a combination of the animal protein fiber with synthetic fiber, such as wool combining with acrylic fiber, or combining natural silk with rayon. Said fiber means top or yarn.

The method of dyeing hairs (such as wool, cony hair, camel hair, cashmere) or its yarn or fabric by using cationic dyes according to the present invention comprises the steps of:

1) circulating a bath containing said fibers or fabrics with water at a temperature of 20~30° C., in which the bath ratio is between 1:30 and 1:50, and the pH value is adjusted to 3~6; adding the compound as formula [1] as a cationic dyeing auxiliary agent in an amount of 1~8 wt. % on the basis of the total weight of the fibers or fabrics, then circulating the bath for 15~20 minutes;

2) introducing cationic dyes into the bath in an amount of 0.01~3 wt. % on the basis of the weight of the fibers or fabrics; after cycling the bath with a pump for 10~15 minutes at ambient temperature, heating the bath to 98~100° C. at a rate of 1~2° C./min, then boiling the bath for 40~60 minutes; cooling the bath to a temperature below 40° C.; washing the dyed fibers or fabrics in clean water at a temperature between 25 to 40° C. to wash off loose color after the residual liquor in the bath has been discharged; and 3) drying the fibers or fabrics.

The following is the detailed method of dyeing the animal hair fibers or the blended yarn or their fabrics according to the present invention:

Pre-treating: The fibers or fabrics, treated with detergents, are fixed into a dyeing machine, then water at a temperature of 20~30° C. is added and circulated with a pump. The bath ratio (the weight ratio of the fiber or fabric to water) is between 1:30 and 1:50. The pH value of the bath is adjusted to 3~6 with the addition of acids, then the compound of formula [1] as a cationic dyeing auxiliary agent as a solution in water is added in an amount of 1~8 wt. % on the basis of the total weight of the fibers or fabrics, then the bath is circulated with a pump for 15~20 minutes.

Dyeing: Formulated cationic dyes are introduced into the bath in an amount of 0.01~2 wt. % and 0.01~3 wt. % on the basis of the fibers or fabrics for dyeing animal hair fiber or its fabrics and for dyeing blended yarn or fabrics containing animal hair fiber, respectively. After cycling the bath with a pump for 10~15 minutes at ambient temperature, preferably 25~28° C., the bath is warmed to 98~100° C. at a rate of 12° C./min, then boiled for 40~60 minutes at that temperature. The bath is then cooled to a temperature below 40° C. The dyed fibers or fabrics are washed by clean water at a temperature between 20 to 40° C. to wash off loose color two or three times after the residual liquor in the bath has been discharged. Then the dyeing step is complete.

The so-called drying step is when the fibers or fabrics are hydro-extracted and oven-dried.

In the pre-treating step, it is preferred to use weak acid to adjust the bath to a weak acid state. Furthermore, considering device corrosion and environmental pollution, acetic acid is most preferred.

When used as a cationic dye auxiliary agent for dyeing and finishing such animal protein fibers as wool and fabrics with cationic dyes, the compound as formula [1] according to the present invention plays a key role, and its amount directly influences the results of dyeing and finishing. It is discovered that if the amount of compound [1] is too small, the rate of dyeing and dyeing quality cannot meet the requirement. But if the amount is too big, the compound as formula [1] and the cation from the cationic dyes will form precipitates which deposit on the surface of protein fibers; consequently, the dyeing performance is adversely affected. Experiments show that when the amount of fibers and dyes and other conditions remain unchanged, the smaller the amount of compound [1] used, the lighter the depth of shade the product has; on the contrary, the larger amount of compound [1] used, the deeper the depth of shade the product has.

In general, the amount of compound [1] is limited between 1 and 8% by weight, based on the weight of the fabric substrate. When dyeing and finishing the fibers with light color, the amount is limited between 1 and 3% by weight; and for the fibers with medium heavy color, the amount is in the range of 5 to 8% by weight.

In addition, the control of pH value in the dyeing and finishing process has a great effect on the texture, glossiness and color stability of the dyed fibers. With a lower pH value, the fibers are accompanied with quickly dyed and high dye takeup, but the strength criteria is lower and uneven dyeing more likely. When the pH value is higher, the fibers will have good strength properties, but a low rate of dyeing and poor brightness. Therefore, for wool, cony hair, cashmere, camel's hair and other fibers, the pH value is preferably selected from a range of 3 to 8.

Before dyeing and finishing such animal protein fibers as wool and fabrics by use of the compound [1] as a cationic dye auxiliary agent, the compound [1] is first dissolved in water at a temperature between 30 and 60° C., with concentration of the solution based on its saturated solution.

The experimental results show that use of the compound [1] of the invention as cationic dye auxiliary agents overcomes the prior difficulties encountered when using cationic dyes for dyeing and finishing such animal protein fibers as wool. And, for blended yarn or fabrics containing animal protein fibers, the stage-dyeing process is no longer necessary. The present invention simplifies the whole dyeing and finishing process, and results in a good dyeing quality. It is also discovered that if the dye depth is the same, the process according to the present invention can reduce the consumption of dyes and thus improve the economic benefits. Furthermore, owing to the fact that in the dyeing and finishing process addition of other auxiliary agents, such as mordant, softeners, diffusing agents, penetrant, and so on, are not needed, environmental pollution caused by discharge of waste liquids is substantially reduced.

The present invention further provides a method for dyeing and finishing natural silk by cationic dyes by using the cationic dye auxiliary agents according to the present invention. The method also includes three processes:

1) circulating the bath which contains fibers or fabrics with water at a temperature of 20~25° C. for 10 to 15 minutes, in which the bath ratio is 1:30 to 1:50, and the pH value is adjusted into a range of 4 to 8; adding the compound [1] into the bath in an amount of 1~8 wt. % on the basis of the total weight of the fibers or fabrics; then circulating the solution for 15~20 minutes;

2) adding cationic dyes into the bath in an amount of 0.01~3% by weight on the basis of the total weight of the fiber or the fabrics; after cycling the bath for 15~20 minutes at ambient temperature, heating the bath to 75~85° C. at a rate of 12° C./min, then sustaining the bath at this temperature for 10~30 minutes; heating the bath to 98~100° C. at a rate of 2~3° C./min, and sustaining it at this temperature for 30~50 minutes, cooling the bath to a temperature below 40° C.; washing the dyed fibers or fabrics by clean water at a temperature between 20 to 35° C. to wash off loose color after the residual liquor in the bath has been discharged; and 3) drying the fibers or fabrics.

In particular, the three steps are:

Pre-treating process: The fibers or fabrics, fine-worsted in advance and treated with detergents, are fixed into a dyeing machine and then washed two to four times with water at a temperature of 20~25° C. for about 10~15 minutes. The bath ratio (weight ratio of the fibers or fabrics to water) is 1:30 to 1:50; pH value is adjusted into a range of 4 to 8 with addition of acids, preferably a weak acid, most preferably acetic acid. A solution of the dissolved compounds [1] (which is dissolved in water at a temperature between 30 and 60° C., with concentration of the solution based on its saturated solution) is added in an amount of 1~8 wt. % on the basis of the fibers or fabrics. Then the solution is circulated with a pump for 15~20 minutes.

Dyeing: Cationic dyes formulated in an amount of 0.01~3%, based on the weight of the fiber or the fabrics is added into the dye vessel. After cycling the bath with a pump for 15~20 minutes at ambient temperature, preferably 20~25° C., the bath is warmed to 75~85° C. at a rate of 1~2° C./min, then sustained at this temperature for 20~40 minutes. Then the bath is warmed to 98~100° C. at a rate of 2~3° C./min, and sustained at this temperature for 30~50 minutes. The bath is cooled to a temperature below 40° C. The dyed fibers or fabrics are washed by clean water at a temperature between 20 to 35° C. to wash off loose color two or three times after the residual liquor in the bath has been discharged.

Drying: The fibers or fabrics are hydro-extracted and oven-dried.

The amounts of the compound [1] are also a key factor which affects the dyeing quality. If the amount is too small, the rate of dyeing is low and the dyeing quality cannot meet the requirements. But if the amount is too big, the compound [1] and the cation from the cationic dyes will form precipitates which deposit on the surface of protein fibers. Consequently, the dyeing performance will be adversely affected.

It is shown that, when dyeing and finishing natural silk and fabrics therefrom with light color, the amount of the compound [1] used as a cationic dye auxiliary agent in the present invention is limited between 1 and 3% by weight on the basis of the fibers or fabrics. And for natural silk and fabrics with medium heavy color, the amount is in the range of 3 to 5% by weight. For natural silk and fabrics with heavy color, the amount is in the range of 5 to 8% by weight.

Due to the use of the cationic dye auxiliary agent, it is possible to dye and finish the natural silk and its fabrics with cationic dyes and to obtain good dyeing quality, high color fastness and bright color. Furthermore, the dyeing process doesn't discharge strong acid and hypertoxic residual liquor, thus environmental pollution is substantially reduced, owing to the fact that no additional auxiliary agents, such as mordant, softeners, diffusing agents, penetrant, fixing agents (particularly such hypertoxic chemicals as NaCN), are needed in the process.

At the same time, great improvements have been made for dyeing and finishing blended yarn and blended fabrics (such as the mixture of hairs and synthetic fibers, e.g., acrylic fiber, as well as the mixture of natural silk and rayon) which can be dyed by a one-step process. On the contrary, owing to the use of different types of dyestuffs, a two-step process is needed in the prior art. For the cationic dye auxiliary agents of the present invention, the advantages for dyeing and finishing blended fibers or textiles thereof are significant, such as time saved for dyeing and finishing, reduced amounts of dyes, and shortening processing procedures, so costs are decreased to a great extent. Therefore, the above methods of dyeing and finishing hair fibers or fabrics provided by the present invention may be extended to blended fibers or fabrics. Examples will be given to illustrate the effectiveness for dyeing blended yards (e.g., acrylic fiber—wool with different wool content) and mixed shameuse (natural silk and rayon).

The following examples illustrate the invention in details without limitation thereto.

EXAMPLE 1

Preparing Sodium Salt of Compound (c) as a Cationic Dye Auxiliary Agent

1) In a reactor, 6.23 kg (0.046 mol) of cyanuric trifluoride (available from dyestuff factory of Shanghai Chemicals Co.) was dissolved into 30 liters office water, and the temperature was controlled at −3° C. 11.79 kg (0.51 mol) of anhydrous sodium p-amino sodiumbenzene sulfonate (available from Tianjin Industrial Chemicals Supply Center) was added with stirring and a reaction initiated. After 10 minutes, a catalyst, i.e., a mixed solution of 8.0 kg sodium hydroxide and 2.0 kg phosphoric acid as well as 40 kg of water, was also introduced into the reactor, so as to increase the pH value of the solution slowly. The reaction was maintained for 4.5 hrs., and the temperature was between −3 and 8° C. After the pH of the reaction solution changed from 1 to more than 5 and held stable, the reaction was continued for 25 to 60 minutes. When the amount of free amine was less than 0.8%, the reaction was stopped, and 15.68 kg of the intermediate was obtained. The yield was 87%.

2) The intermediate was moved into the second reactor, adding a solution of β-aminonaphthalene (conc. 35% by weight, available from Jilin Chemicals Co.) which included 7.36 kg (0.51 mol) β-aminonaphthalene so that the molar ratio of cyanuric trifluoride to β-aminonaphthalene was 1.0:1.1. Then a mixed solution of sodium hydroxide and phosphoric acid was added (as in step 1). The reaction was carried out for 4 hrs. at pH 4~8, temperature 25~50° C. as well as under a pressure of 0~0.01 MPa. After the pH value of the reaction solution remained substantively unchanged, the reaction was continued for 2 hrs. and halted. Then the pH value was adjusted to around 7 by using acetic acid. 21.2 kg of product was finally obtained through discharging, filtering, drying and grinding. The yield of product was 92%.

The aforementioned procedures were repeated by using the same mole of cyanuric trifluoride instead of cyanuric trifluoride. Sodium salt of compound (d) was obtained, yield 91%.

EXAMPLE 2

Preparation of the Compound (b) as a Cationic Dye Auxiliary Agent

1) The procedure 1) in Example 1 was repeated, except that 5.86 kg of cyanuric trichloride (available from dyestuffs factory of Shanghai Chemicals Co.) and 7.45 kg of p-aminobenzenen sulfonic acid (available from Tianjin Industrial Chemicals Supply Center) were used. Herein, reaction temperature was between −2 and 1° C., the reaction pressure was at 0.005 MPa, pH=5~7, and the reaction lasted for 4 hrs.

2) The procedure 2) in Example 1 was repeated, except that 4.98 kg of β-naphthol (available from Jilin Chemicals Co.) was used.

Herein, reaction temperature was between 25 and 43° C., the reaction pressure was at 0.02 MPa, pH=2~8, and the reaction lasted for 5 hrs. 17.7 kg of final product was obtained.

The aforementioned procedures were repeated by using the same mole of cyanuric trifluoride instead of cyanuric trichloride. Compound (a) was obtained, yield 94%.

The aforementioned procedures were repeated by using the same mole of (α-naphthol instead of β-naphthol. Compound (e) was obtained, yield 95%.

EXAMPLE 3

Preparation of the Compound (f) as a Cationic Dye Auxiliary Agent

1) The procedure 1) as in Example 1 was repeated, except that 3.4 kg of cyanuric trifluoride and 5.75 kg of p-aminobenzene sulfonic acid, which were dissolved in 30 liters of soft water, were used. Herein, reaction temperature was −1° C., the reaction pressure was between 0 and 0.011 MPa, pH=4~8, and the reaction lasted for 4.2 hrs.

2) The procedure 2) as in Example 1) was repeated, except that 4.86 kg of α-aminonaphthalene (Jilin Chemicals Co.) was used. Herein, the reaction temperature was between 30 and 50° C., the reaction pressure was at 0~0.03 MPa, pH=3~9, and the reaction lasted for 4.6 hrs. 13.31 kg of final product was obtained.

The aforementioned procedures were repeated by using the same mole of cyanuric trichloride instead of cyanuric trifluoride. Compound (g) was obtained, yield 93%.

In the following examples, all cationic dyestuffs were obtained from Shanghai BASF.

EXAMPLE 4

Dyeing Wool 0.03 g of cationic dye auxiliary agents prepared in Example 1 were dissolved into 20 ml water, the solution was then added into a beaker containing 120 ml of soft water, and the pH value was adjusted to about 4 with steady stirring. 3 g of wool yarn (Xinjiang wool, Tianjin Dongya Woolen Mill Group Co.) treated with detergent was introduced into the beaker, then a solution of cationic dyes (0.006 g Cationic Brilliant Red X-5GN, 0.0009 g Cationic Brilliance Flavine X-10GFF) was added and mixed homogeneously by stirring, continuously tumbling the fibers. The temperature of the solution increased at a rate of 1° C. per minute from room temperature. When arriving at 98° C., the temperature was maintained and the solution was boiled for 40 minutes. Then the temperature was decreased to below 40° C. After discharging the residual liquor and washing the wool fiber three times with clean water, the wool fiber was taken out from the dye vessel and hydro-extracted and oven-dried. Then a product with pink color was obtained. The dyeing performance figures are listed in Table 1.

EXAMPLE 5

Dyeing Wool

The procedure as in Example 4 was repeated, except that 3 g of wool yarn (Australian wool, Tianjin Dongya) and 0.15 g of cationic dye auxiliary agents prepared in Example 3 were used. The used cationic dyes comprised 0.0351 g Aizen Cathilon Red S-GLH, 0.036 g Aizen Cathilon Blue GLH and 0.028 g Aizen Cathilon Yellow 3GLH; pH value was at 5.5, and the solution was boiled at 99~100° C. for about 50 minutes. Then a product with navy blue color was obtained. The dyeing performance figures are listed in Table 1.

EXAMPLE 6

Dyeing Blended Yarn of 70% Wool and 30% Acrylic Fiber 0.09 g of cationic dye auxiliary agents prepared in Example 1 were dissolved into 50 ml water; the solution was then added into a beaker containing 150 ml of soft water. A mixed solution of cationic dyes (0.0279 g of Cationic Yellow 7GL, 0.0351 g of Cationic Red 2GL, 0.0297 g of Cationic Blue 2RL and 0.003 g of Basic Orange) was introduced. After mixed homogeneously by stirring, 3 g of blended yarn (available from Yizheng Woolen Mill) was added into the beaker for dyeing. The temperature of the solution increased at a rate of 1° C./2 minutes from room temperature; when up to 80° C., the temperature was held for 20 minutes. Then the temperature of the solution increased again at a rate of 1° C. per minute to 100° C., and the solution was boiled out at 100° C. for 50 minutes. After discharging the residual liquor and washing the substrate three times with clean water, the wool fibers were taken out from the beaker, hydro-extracted and oven-dried. Then a product with black color was obtained. The dyeing performance figures are listed in Table 1.

EXAMPLE 7

Dyeing Blended Yarn of 90% Wool and 10% Acrylic Fiber

The procedure as in Example 6 was repeated, except that 3 g of blended yarn (90% wool and 10% acrylic fiber) (available from Tianjin Dongya) and the sodium salt compound (a) prepared in Example 2 (3 wt. % based on the total weight of the yarn) were used. The used cationic dyes comprised 0.0087 g of Cationic Yellow X-8GL, 0.00705 g Cationic Red X-GRL and 0.003 g of Cationic Blue. Then a product the color of light tan was obtained. The dyeing performance figures are listed in Table 1.

EXAMPLE 8

Dyeing Cony Hair

The procedure as in Example 4 was repeated, except that 3 g of cony hair (available from Hangzhou Silk Co.) and 0.03 g of a cationic dye auxiliary agent prepared in Example 2 were used, and the used cationic dyes comprised 0.012 g of Cationic Blue X-GB and 0.0009 g of Cationic Brilliance Flavine X-10GFF; pH value was at 4.5. The solution was boiled out at 100° C. for 60 minutes. Then a product the color of pale yellowish green was obtained. The dyeing performance figures are listed in Table 1.

TABLE 1

| | | | | Textile Industry Standard FZ71004-91 | | | | | |
|---|---|---|---|---|---|---|---|---|---|
| Item | | Unit | Test Method | Good quality product | Ex. 4 | Ex. 5 | Ex. 6 | Ex. 7 | Ex. 8 |
| Color fastness to washing | Color change | Grade | GB5713 | ≧4 | 4 | 4 | 4 | 4 | 4 |
| | Staining for wool cloth | Grade | GB5713 | ≧3 or 4 | 4 | 3–4 | 3–4 | 3–4 | 3–4 |
| | Staining for cotton cloth | Grade | GB5713 | ≧3 or 4 | 4 | 4 | 4 | 4 | 4 |
| Soaping fastness | Color change | Grade | GB/T12490 | ≧3 or 4 | 4 | 4 | 4 | 4 | 4 |
| | Staining for wool cloth | Grade | GB3921 | ≧4 | 4 | 4 | 4 | 4 | 4 |
| | Staining for cotton cloth | Grade | GB3921 | ≧3 or 4 | 3 | 3–4 | 3–4 | 3–4 | 3–4 |
| Fastness to perspiration | Color change | Grade | GB3922 | ≧3 | 3 | 3 | 3 | 3 | 3 |
| | Staining for wool cloth | Grade | GB3922 | ≧3 | 3 | 3 | 3 | 3 | 3 |
| | Staining for cotton cloth | Grade | GB3922 | ≧3 | 3 | 3 | 3 | 3 | 3 |
| Rubbing fastness | Dry rubbing | Grade | GB3920 | ≧3 or 4 | 4 | 4 | 4 | 4 | 4 |
| | Wet rubbing | Grade | GB3920 | ≧3 | 3 | 3 | 3 | 3 | 3 |
| Color fastness to light | >1/12 standard solution | Grade | GB8427 | ≧4 | 4 | 4 | 4 | 4 | 4 |
| | <1/12 standard solution | Grade | GB8427 | ≧3 | 3 | 3 | 3 | 3 | 3 |

EXAMPLE 9

Dyeing Skein Silk

1) After adding 120 ml of soft water into a 250 ml-volume beaker and adjusting the pH value of the water to 5, the solution of the compound prepared in Example 1 was introduced into the beaker (the solution contained 6 mg of the compound prepared in Example 1 as a cationic dye auxiliary agent) with stirring. 3 g of skein silk (available from Jiaxing Deli Dyeing and Printing Co., Ltd.) treated with detergent was put into the beaker.

2) Then the mixed solution of 0.022 g of Cationic Yellow X-8GL and 0.0024 g of Cationic Red X-2GL (the two dyes were dissolved with 20 ml of boiling water, respectively, then mixed together) was added with continuous stirring. The temperature of the solution increased at a rate of 1° C. per minute from 20° C. to 80° C., and held at 80° C. for 20 minutes. Then the temperature of the solution continued to increase at a rate of 2~3° C. per minute from 80° C. to 100° C. and held at 100° C. for 30 minutes. Then the temperature decreased to below 40° C., and the skein silk was washed three times with clean water.

3) Hydro-extracting and oven-drying the skein silk was performed. Then a product with yellowish pink color was obtained. The color fastness quality is listed in Table 2.

EXAMPLE 10

Dyeing Skein Silk 3 g of skein silk was taken (from Jiaxing Deli) and the procedures repeated as in Example 8, in which the pH value was 5.5, and 9 mg of the compound prepared in Example 2 was used as a cationic dye auxiliary agent.

The cationic dyes used comprised 0.028 g of Aizen Cathilon Yellow 3GLH, 0.035 g of Aizen Cathilon Red BLH, and 0.036 g of Aizen Cathilon Blue GLH.

The heating schedule in the dyeing process was as follows: beginning with room temperature, increasing the temperature of the solution at a rate of 1° C. per minute to 75° C., holding for 20 minutes at 75° C.; then continuing to increase the temperature at a rate of 3° C. per minute to 98° C., holding for 40 minutes at 98° C. Finally, a product with dark blue color was obtained. The color fastness quality is listed in Table 2.

TABLE 2

| | | | | Textile Industry Standard FZ4300-91 | | |
|---|---|---|---|---|---|---|
| Item | Color fastness to | Unit | Test method | First quality product | Ex. 9 | Ex. 10 |
| washing water perspiration | Color change | Grade | GB250 GB3921 | 3–4 | 3–4 | 3–4 |
| | Staining | Grade | GB5713 GB3922 | 2–3 | 2–3 | 2–3 |
| light | | Grade | GB8427 (xenon arc) | 3 | 3 | 3 |
| rubbing (dry) | | Grade | GB3920 | 2–3 | 2–3 | 2–3 |

EXAMPLE 11

Dyeing Habutai Silk 3 g of habutai silk (from Hangzhou Silk Co.) was used to repeat the procedures as in Example 9, in which the pH value was 5, and 9 mg of the product [compound (f)] prepared in Example 3 was used as a cationic dye auxiliary agent.

The cationic dyes used comprised 0.016 g of Cationic Brilliance Flavine X-10GFF and 0.003 g of Cationic Red X-GRL.

The heating schedule in the dyeing process was the same as in Example 9. Then a product with orange yellow color was obtained. The color fastness quality is listed in Table 3.

EXAMPLE 12

Dyeing Crepe De Chine Silk 3 g of crepe de chine silk (Hangzhou Silk Co.) was used and the procedures as in Example 9 were repeated, except that the pH value was about 5.5, and 12 mg of the product [compound (c)] from Example 1 was used as a cationic dye auxiliary agent.

The cationic dyes used comprised 0.0159 g of Aizen Cathilon Yellow X-8GL, 0.0219 g of Aizen Cathilon Red X-GRL, and 0.005 g of Aizen Cathilon Blue X-GRRL.

The heating schedule in the dyeing process was as follows: beginning with 20° C., increasing the temperature of the solution at a rate of 1° C. per minute to 70° C., holding for 20 minutes at 70° C.; then continuing to increase the temperature at a rate of 2~3° C. per minute to 100° C., holding for 60 minutes at 100° C. Then a product with rust color was obtained.

The color fastness quality is listed in Table 3

TABLE 3

| Item | Color fastness to | Unit | Test method | Textile Industry Standard ZBW43004-90 First quality product | Ex. 11 | Ex. 12 |
|---|---|---|---|---|---|---|
| washing water perspiration | Color change | Grade | GB250 | 3 | 3 | 3 |
| | Staining for silk fabric | Grade | GB3921 | 2–3 | 2–3 | 2–3 |
| | Staining for cotton cloth | Grade | GB3922 | 2–3 | 2–3 | 2–3 |
| rubbing (dry) | | Grade | GB3920 | 2–3 | 2–3 | 2–3 |
| light | | Grade | GB8427 (xenon arc) | 3 | 3 | 3 |

EXAMPLE 13

Dyeing Natural-rayon Mixed Shameuse 5 g of natural-rayon mixed shameuse (Hangzhou Silk Co.) was used and the procedures as in Example 12 were repeated, except that the product [compound (f)] from Example 3 was used as a cationic dye auxiliary agent in an amount of 3%, based on the total weight of the fabric. The used cationic dyes comprised 0.03 g of Cationic Brilliance Flavine X-10GFF and 0.085 g of Cationic Blue X-GB. The color of the final product was pale yellowish green with a white pattern remaining.

What is claimed is:
1. A compound of formula [1],

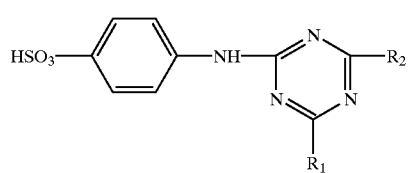

wherein $R_1$, represents Cl, F; $R_2$, is α- or β-naphthylamino, or α- or β-naphthoxy, and its alkali salt.

2. The compound according to claim 1, wherein the compound is selected from the group consisting of the following compounds (a)–(g) and sodium salt thereof:

(a)

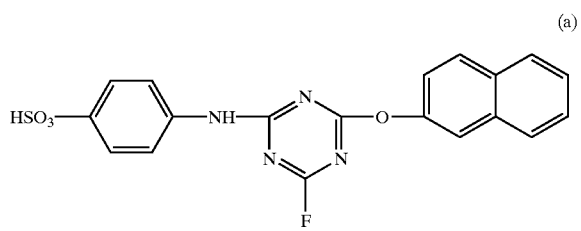

(b)

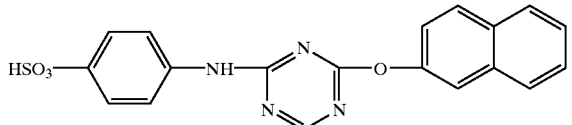

(c)

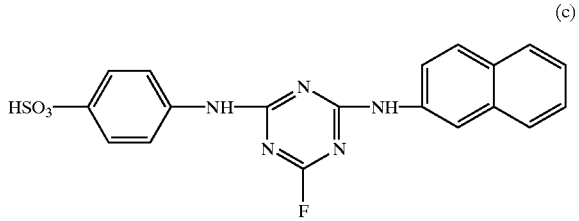

(d)

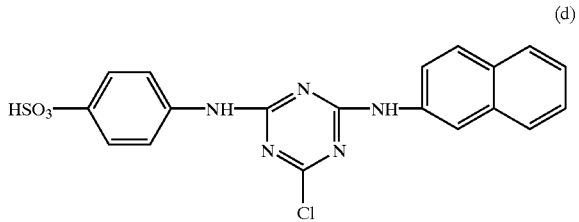

(e)

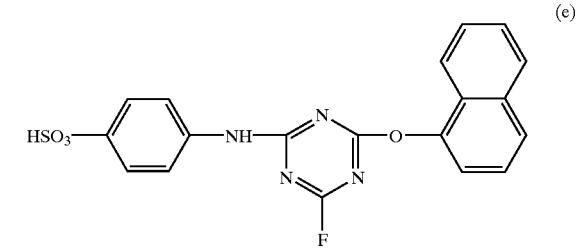

(f)

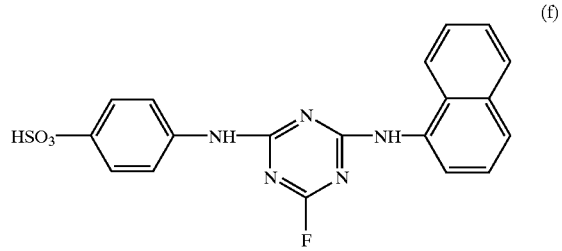

(g)

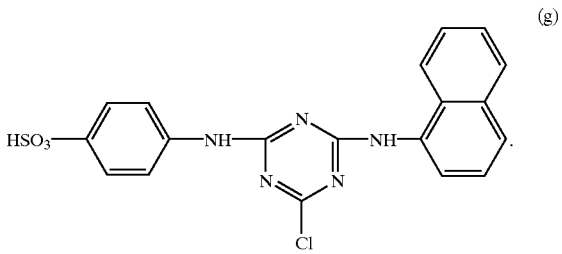

3. A method for preparing the compound of formula [1] and its salt as claimed in claim 1

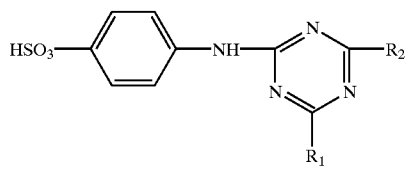

[1]

wherein $R_1$, represents Cl, F; $R_2$, is α- or β-naphthylamino, or α- or β-naphthoxy, comprising the following steps:
(a) Dissolving cyanuric trihalide into ice water in a reaction vessel, then adding p-aminobenzene sulfonic acid or its alkali salt slowly to initiate the reaction, and controlling the temperature between −3 and 10° C., and the pressure between 0 and 0.05 MPa; adding a mixed solution of sodium hydroxide and phosphoric acid as a catalyst and maintaining the reaction for 3~5 hrs; obtaining an intermediate of formula [4] when the pH value of the reaction solution exceeds 5 and the amount of free amine is less than 0.8%;

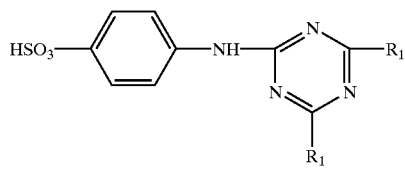

[4]

(b) Moving the intermediate as formula [4] into another reaction vessel, then adding a solution of compound $HR_2$ as well as a mixed solution of sodium hydroxide and phosphoric acid as a catalyst into the same vessel; sustaining the reaction for 4~5 hrs. at a temperature of 15~50° C. and under a pressure of 0~0.03 MPa as well, and a pH value of 5~10; then adjusting the pH value to about 7, and obtaining the compound of formula [1] and its salt through discharging, filtering, drying and grinding.

4. The method of claim 3, wherein the molar ratios of the three raw materials are: cyanuric trihalide/p-aminobenzene sulfonic acid or its salt/$HR_2$=1.0: (1.10~1.3): (1.0~1.25).

5. A method for dyeing animal protein fiber or fabric, or blended yarn or its fabric containing animal protein fiber with cationic dyestuffs comprising the step of pretreating said fiber or fabric with a compound of formula [1] as claimed in claim 1 as a cationic dye auxiliary agent.

6. A method according to claim 5, wherein said method comprises the following steps:

1) circulating a bath containing said fiber or fabric and water at a temperature of 20~30° C., in which the bath ratio is between 1:30 and 1:50, and the pH value is adjusted to 3~6 with addition of acids; adding the compound as formula [1] as a cationic dyeing auxiliary agent in an amount of 1~8 wt. % on the basis of the weight of the fiber or fabric, then circulating the bath for 15~20 minutes;

2) introducing cationic dyes into the bath in an amount of 0.01~3 wt. % on the basis of the weight of the fiber or fabric; after cycling the bath for 10~15 minutes at ambient temperature, heating the bath to 98~100° C. at a rate of 1~2° C./min, then boiling the bath for 40~60 minutes at that temperature; cooling the bath to a temperature below 40° C.; washing the dyed fibers or fabrics with clean water at a temperature between 25 to 40° C. to wash off loose color after the residual liquor in the bath has been discharged; and 3) drying the fibers or fabrics.

7. The method of claim 6, wherein said animal protein fiber is selected from the group consisting of wool, cony hair, camel hair, cashmere, and camel's hair fabric made thereof or its blended yarn or fabric containing aforementioned animal protein fiber and synthetic fiber.

8. A method according to claim 5, wherein said method comprises the following steps when natural silk fiber or fabric, or blended yarn as fabric of natural silk and rayon is dyed:

1) circulating the bath which contains said fiber or fabric and water at a temperature of 20~25° C. for 10 to 15 minutes, in which the bath ratio is 1:30 to 1:50, and the pH value is adjusted into a range of 4 to 8; adding the compound [1] into the bath in an amount of 1~8 wt. % on the basis of the weight of the fiber or fabric; then circulating the solution for 15~25 minutes;

2) adding cationic dyes into the bath in an amount of 0.01~3% by weight on the basis of the total weight of fiber or fabric; after cycling the bath for 15~20 minutes at ambient temperature, heating the bath to 75~85° C. at a rate of 1~2° C./min, then sustaining the bath at this temperature for 20~40 minutes; heating the bath to 98~100° C. at rate of 2~3° C./min, and sustaining it at this temperature for 30~50 minutes; cooling the bath to a temperature below 40° C.; washing the dyed fibers or fabrics by clean water at a temperature between 20 to 35° C. to wash off loose color after the residual liquor in the bath has been discharged; and 3) drying the fibers fabrics.

* * * * *